United States Patent [19]

Huang et al.

[11] Patent Number: 4,731,324

[45] Date of Patent: Mar. 15, 1988

[54] VIRAL LYSIS ASSAY

[75] Inventors: Anthony H. Huang, Mountain View; Brenda Heath; Francis J. Martin, both of San Francisco, all of Calif.

[73] Assignee: Cooper-Lipotech, Inc., Menlo Park, Calif.

[21] Appl. No.: 612,421

[22] Filed: May 21, 1984

[51] Int. Cl.[4] .................. C12Q 1/70; C12N 7/00; G01N 33/554; G01N 33/555

[52] U.S. Cl. .................... 435/5; 435/235; 435/748; 436/501; 436/519; 436/520; 436/522; 436/829

[58] Field of Search ............... 436/512, 501, 519, 520, 436/522, 523, 800, 819, 829; 435/5, 7, 235, 236, 238, 948

[56] References Cited

U.S. PATENT DOCUMENTS 4,342,826  8/1982  Cole ........................... 436/829 X
4,483,929  11/1984  Szoka .......................... 436/512 X

OTHER PUBLICATIONS

Sinha, D. et al., Biochem. Biophys. Res. Commun., 90, No. 2: 554–560, (1979).
Tomasi, M. et al., FEBS Letters, 143, No. 2: 252–256, (1982).
Heath, T. et al., (1983), Exp. Cell Res., 149: 163–175.
Bankert, R. et al., (1979), Journ. of Immunol., 123, No. 6: 2466–2473.
Sekiguchi, K. et al., (1978), PNAS 75, No. 4: 1740–1744.
Oku, N. et al., (1982), Virology, 116: 419–427.
Huang, A. et al., (1980), Journ. of Biol. Chem., 255, No. 17: 8015–8018.

Primary Examiner—Esther M. Kepplinger
Assistant Examiner—Jack Spiegel
Attorney, Agent, or Firm—Ciotti, Murashige, Irell & Manella

[57] ABSTRACT

A viral lysis immunoassay system and method. The system includes hemolytic particles carrying non-viral, anti-analyte molecules, lysable target cells which are devoid of surface molecules capable of binding to endogenous viral surface molecules, and foreign binding molecules added to the target cells. The binding molecules, which may be either analyte molecules or analyte-related molecules attached to the target cell surfaces, function to bind the particles to the cells, to initiate cell lysis and the release of encapsulated reporter molecules from the cells. The analyte to be assayed may be one adapted to bridge the virus particles to analyte-related molecules carried on the cell surfaces, or one which competes with target-cell molecules for binding to the particle anti-analyte molecules.

6 Claims, No Drawings

VIRAL LYSIS ASSAY

BACKGROUND AND SUMMARY

The present invention relates to an immunoassay system and method which are based on immunospecific target-cell lysis by hemolytic virus particles.

The following publications are referred to by the corresponding number herein:
1. Choppin, P. W., and Scheid, A., Rev. Infect. Dis., 2:40 (1980)
2. Shimizu, Y. K., et al., Virology, 71:48 (1976)
3. Nakanishi, M., et al., Exp. Cell Res., 142:95 (1982)
4. Heath, T. D., et al., Exp. Cell Res., 149:163 (1983)
5. Kundrot, C. E., et al., Proc. Nat. Acad. Sci. USA, 80:1608 (1983)
6. Oku, N., et al., Virology, 116:419 (1982)
7. Heath, T. D., et al., ibid.
8. Tomasi, M., et al., Febs. Letts., 143:252 (1982)
9. Curman, B., et al., J. Biol. Chem., 255:7820 (1980)
10. Heath, T. D., et al., Biochimica et Biophysica Acta, 640:66 (1981)
11. Martin, F. J., et al., Biochemistry, 20:4229 (1981)
12. Martin, F. J., et al., J. Biol. Chem., 257:286 (1982)
13. Huang, A., et al., J. Biol. Chem., 255:8015 (1980)
14. Lapidot, Y., et al., J. Lipid Res. 8:142 (1967)
15. Hosaka, Y., et al., Intervirology, 10:70 (1977)
16. Homma, M., J. Virol., 9:829 (1972)

An important property of hemolytic viruses is the ability to bind specifically to and fuse with target host cells (reference 1). Under isotonic or slightly hypotonic conditions, fusion with the hose cell membrane can produce cell lysis, as evidenced, for example, by release of hemoglobin from lysed erythrocytes (reference 2). The hemolytic viruses, as exemplified by Sendai virus, contain two surface glycoproteins which have been implicated in the cell binding and fusion events: an HN glycoprotein, so named because of its apparent hemagglutinating and neuraminidase activities involved in virus binding to and cleavage of a sialic acid moiety associated with the host cell receptor; and an F glycoprotein, so named because of its apparent role in fusion of the attached virus with the host cell membrane (reference 3).

The interaction of hemagglutinating viruses with target cells have been studied in a number of surface-modified and/or artificial systems. Early studies of this type showed that the binding and lytic activity of hemolytic virus, e.g. Sendai virus, toward erythrocytes is substantially eliminated when the erythrocyte target cells are desialylated by treatment with neuraminidase (reference 4). Kundrot, et al. demonstrated that lipid vesicles (liposomes) containing cholesterol and surface-bound glycophorin (the Sendai-virus receptor on human erythrocytes) are susceptible to lysis by intact Sendai virus, but not by virus which have been inactivated by trypsin digestion (reference 5). Similarly, Oku, et al. have observed that liposomes composed of phosphatidylcholine (PC) and surface-bound glycophorin were damaged by native, but not by trypsin-treated hemagglutinating virus (reference 6). The above studies indicate that cell lysis is mediated by specific binding interaction between one or more trypsin-labile viral glycoproteins and cell-bound glycophorin.

More recent studies have examined the nature of the virus/cell binding specificity in the cell lytic reaction. In one such study, Heath, et al. have shown that Sendai virus modified to contain surface-bound anti-glycophorin can hemolyze desialylated human erythrocytes, the lytic reaction presumably being mediated by binding of virus-bound anti-glycophorin to cell-surface glycophorin (reference 7). It has also been reported that virus particles having surface-bound anti-erythrocyte antibodies are capable of lysing neuraminidase-treated red blood cells (reference 8). The latter report suggests that cell lysis can be mediated by a virus/cell binding event between virus-bound anti-erythrocyte antibodies and non-glycophorin erythrocyte surface antigen(s). However, as emphasized in the report, the "targeted virus" produced only about 1% to 10% of the hemolytic activity obtained with untreated virus and normal erythrocytes.

The present invention includes a novel immunoassay system in which hemolytic virus particles carrying non-viral, analyte-binding molecules interact specifically with foreign binding molecules anchored to target cells, to produce efficient target cell lysis. In some cases, the efficiency of cell lysis observed is substantially 100% that of normal viral-mediated cell lysis involving native viral and target cell components. The system of the invention includes hemolytic particles having surface-bound paramyxovirus HN and F glycoproteins, and surface arrays of non-viral, anti-analyte molecules. Target cells in the system are substantially devoid of surface receptors capable of binding to such HN or F proteins, and are prepared to include an encapsulated reporter which is detectable upon cell lysis. Foreign binding molecules anchored to the cells function to attach the hemolytic particles to the cell surfaces, to initiate target cell lysis, as evidenced by reporter release from the cells.

The immunoassay system may be used in two general types of reactions for the determination and/or quantitation of soluble analytes. In one reaction, referred to herein as a competitive-inhibition reaction, the foreign binding molecules include analyte-like molecules i.e., analyte or analyte analogue molecules which are attached to the cell surfaces and which are capable of competing with the analyte for binding to the particle anti-analyte molecules. A greater concentration of analyte molecules in the assay mixture therefore produces proportionately less binding of the hemolytic particles to the target cells and less released reporter. The competitive inhibition assay can be used for determination of analytes capable of one (monovalent) or more (multivalent) binding reactions. In the second type of reaction, referred to herein as a sandwich-type reaction, the foreign binding molecules are soluble analyte molecules capable of reacting cooperatively both with analyte-related molecules attached to the target cell surfaces, and with particle anti-analyte molecules, to bind the particles to the cells by analyte bridging. The soluble analyte molecules in this type of reaction are necessarily multivalent, i.e. contain at least two specific binding sites which can participate in cooperative binding to the target cell and particle surface molecules. The cell lysis immunoassay reactions, and particularly the sandwich-type reaction, have the potential for high assay sensitivity, since relatively few analyte-related binding events on the target cell surface can lead to the release or expression of a large number of reporter molecules.

The reporter which is encapsulated in the target cells may include cell-endogenous molecules, such as hemoglobin reporter molecules contained within surface-modified erythrocytes. Alternatively, the target cells may be prepared to encapsulate exogenous reporter molecules such as enzymes, chromophores, fluorogenic compounds or stable electron paramagnetic compounds. With many of the non-chromophoric reporter molecules just mentioned, released reporter can be readily detected in a suspension of target cells, affording the advantage that the complete reaction procedure—including the analyte-dependent binding reaction between the particles and cells, and measurement of released reporter form lysed target cells—can be performed in a single assay mixture, without the requirement for an intervening fractionation step. Immunoassays which can be carried out in this fashion are generally referred to as homogeneous immunoassays.

Also included in the invention is an immunoassay kit for the determination and/or quantitation of a soluble monovalent or multivalent analyte. The kit includes the hemolytic particles and target cells described above.

The invention further includes a method for the determination of a soluble analyte, including the steps of (1) providing hemolytic virus particles and lysable cells of the type described above; (2) reacting the virus particles and cells with a soluble analyte, to bind virus particles to the cells in proportion to the amount of analyte present; and (3) determining the extent of cell lysis.

One general object of the present invention is to provide a novel viral lysis immunoassay for determination of soluble monovalent and multivalent analytes.

Another object of the invention to provide a simple, homogeneous immunoassay for determination of such analytes.

Yet another object of the invention is to provide such an immunoassay which utilizes components which are easily prepared and stable on storage.

These and other objects and features of the present invention will become more fully apparent from the following detailed description of the invention.

DETAILED DESCRIPTION OF THE INVENTION

The present invention includes an immunoassay system for the determination of soluble monovalent or multivalent analytes. The system includes hemolytic particles, whose preparation and important features are described in Section I, and lysable target cells whose preparation and features are detailed in Section II. Immunoassay methods employing the assay system components for the determination of soluble analytes are described in Section III.

I. Preparing Hemolytic Particles

The hemolytic particles of the invention are defined as having a lipid bilayer surface, surface-bound HN and F paramyxovirus glycoproteins, and a surface array of non-viral, anti-analyte molecules which are anchored to the particle bilayer surfaces by lipophilic moieties. The particles are preferably prepared from a selected paramyxovirus, such as Sendai virus, which is surface-modified, according to methods described below, to include surface arrays of the anti-analyte molecules. Although the invention will be illustrated herein with particular reference to Sendai hemolytic virus, other hemolytic viruses which are known to bind to and lyse biological target cells are suitable for use in the invention. Methods for culturing and harvesting such paramyxoviruses are well known, as illustrated by a standard culture technique followed in Example I.

The anti-analyte molecules carried on the particle surfaces are adapted for specific, high-affinity binding to analyte and analyte-like molecules. Specifically, the analyte and anti-analyte molecules are opposite members of a binding pair composed of a ligand having one or more specific epitopic features, and an anti-ligand which recognizes such features to bind the ligand specifically and with high affinity. Binding pairs which are contemplated in the present invention include antigen-/antibody, immunoglobulin/protein A, carbohydrate/-lectin, DNA hybrid pairs, biotin/avidin and hormone/-hormone-receptor protein binding pairs, where the anti-analyte molecules may be selected from either member of the ligand/anti-ligand pair. More generally, the analyte-binding molecules may include fragments or portions of molecules which are capable of participating in specific, high-affinity binding with opposite members of a binding pair. For example, in an antibody/antigen pair, the anti-analyte molecules may include antigen-binding Fab' or $F(ab')_2$ antibody fragments.

As indicated above, the analyte-binding molecules are anchored to the particle surfaces by lipophilic moieties. This type of attachment is distinguished specifically from molecule attachment to particle surfaces by direct covalent coupling to endogenous virus envelope proteins, such as HN or F proteins. The lipophilic moiety in an anti-analyte molecule may include a lipophilic region or portion of the molecule, such as is present in a lipophilic antigen—for example cardiolipin—and in certain membrane proteins having known hydrophobic regions (reference 9). In the more typical case, a selected lipid is coupled to an anti-analyte molecule by covalent attachment to form the lipid moiety.

Several reaction methods for coupling biomolecules, and particularly large biomolecules such as proteins, covalently to lipids are known. One method involves Schiff-base formation between an aldehyde group on a lipid, typically a phospholipid, and a primary amino acid on the anti-analyte. The aldehyde group is preferably formed by periodate oxidation of the lipid. The coupling reaction, after removal of the oxidant, is carried out in the presence of a reducing agent, such as dithiothreitol (reference 10). Typical aldehyde-lipid precursors suitable in this method include lactosylceramide, trihexosylceramide, galactocerebroside, phosphatidylglycerol, phosphatidylinositol and gangliosides. Because the coupling reaction employs a reducing agent which would act to inactivate HN viral protein, the anti-analyte/lipid conjugate is preferably synthesized before the lipid moiety is introduced into the membrane.

A second general coupling technique is applicable to thiol-containing anti-analyte molecules, and involves formation of a disulfide or thioether bond between a lipid and the anti-analyte. In the disulfide reaction, a lipid amine, such as phosphatidylethanolamine, is modified to contain a pyridylditho derivative which can react with an exposed thiol group in the anti-analyte. The reader is referred to reference 11 for a detailed discussion of reaction conditions used in the method. The thioether coupling method, which described in reference 12, is carried out by forming a sulfhydryl-reactive phospholipid, such as N-(4)P-maleimidophenyl(butyryl)phosphatidylethanolamine (MPB-PE), and reacting the lipid with the thiol-containing anti-analyte to form an essentially reversible thioether bond between the anti-analyte thiol group and the lipid maleimide group. In both sulfhydryl coupling methods, the coupling reaction may be carried out before incorporation of the lipid group into the bilayer, to minimize inactivation of the viral glycoproteins by thiol-reactive lipid.

Another method for covalently attaching an anti-analyte to a lipid group has been reported in reference 13, and generally involves reacting the anti-analyte with a lipid which has been derivatized to contain an activated ester of N-hydroxysuccinimide. The reaction is typically carried out in the presence of a mild detergent, such as deoxycholate. Like the reactions described above, this coupling reaction is preferably performed prior to incorporating the lipid into the virus bilayer, to minimize viral protein inactivation by the activated lipid components. Example I below describes a procedure for coupling the N-hydroxysuccinimide ester of palmitic acid to anti-human IgG antibody in the presence of 2% deoxycholate. Example II describes the derivatization of anti-phthalate antibody with palmitic acid to form an antibody/palmitic acid conjugate.

In a preferred method for attaching free lipids or lipid/anti-analyte conjugates to viral surface membranes, the lipid or conjugate is added to a suspension of native hemolytic virus particles under conditions which allow diffusion of the lipid or lipid moiety in the conjugate into the virus membrane. The diffusion reaction likely involves lipid exchange between a micellar or other ordered lipid state and the viral lipid bilayer membrane. The diffusion reaction is usually carried out in a low concentration of detergent, such as deoxycholate or octyl glucoside, to accelerate the exchange reaction. After an incubation period of up to several hours, the hemolytic particles are separated from the detergent and unbound lipid or lipid conjugate, e.g., by centrifugation.

The lipid or lipid conjugate is added to the virus particles in an amount selected to achieve a desired surface concentration of anti-analyte molecules created on the hemolytic particles. The study reported in Example I shows that approximately 50% of an antibody/palmitic acid couple becomes incorporated into hemolytic virus particles during overnight incubation of 37° C. in the presence of 0.012% deoxycholate. As will be seen in Table I of this example, surface concentrations of between about 20 and 100 micrograms (ug) of antibody per milligram (mg) of viral protein are readily achieved by this incubation procedure. A surface concentration of anti-phthalate antibody/palmitic acid conjugates of between about 6–12 ug antibody per mg of viral protein was achieved in the procedure of Example II. It is noted that in both Examples I and II, the antibody preparations used in forming the antibody/lipid conjugates were immunopurified antibody mixtures containing between about 50% to 80% specific anti-analyte antibodies. Thus the amount of anti-analyte molecules attached to the virus surfaces is a major fraction of the total antibodies attached. The experiment reported in Example X, involving direct binding of virus-bound antibody to target cell antigen indicates that the extent of target cell lysis produced by hemolytic particles is substantially independent of the virus antibody surface concentration, above about 20 ug of antibody per mg of viral protein. Further experiments indicate that a total of up to about 200 ug antibody protein per mg viral protein can be incorporated into the virus, by the method of forming an antibody/fatty acid conjugate, and diffusing this conjugate into the virus in the presence of detergent. It can be appreciated from the above that at a surface concentration of 200 ug antibodies per mg viral protein, an antibody mixture containing only 5–10% anti-analyte antibodies would provide a concentration of specific antibodies sufficient to produce maximal analyte-specific cell lysis.

It is seen from the above that three considerations will govern the choice of lipid forming the lipophilic moiety in the anti-analyte/lipid conjugates: (1) the presence of a reactive group which can be used to couple the anti-analyte to the lipid; (2) solubility characteristics of the lipid which will influence its rate of diffusion into the virus bilayer surface, and (3) the ability of the viral particles to accommodate the lipid at the required surface concentration of anti-analyte molecules. The latter consideration is especially important where the specific anti-analyte molecules to be attached constitute only a small fraction of the total number of non-viral molecules bound to the particles as in an impure antibody mixture. With regard to the latter consideration, it has been observed in experiments conducted in support of this application that viral particles containing a relatively high concentration of an added ganglioside conjugate have considerably reduced lytic activity. This effect may be due to the ability of gangliosides to prevent the fused viral membrane from rupturing under normal cell-lysis conditions.

One preferred lipid for use in attaching anti-ligand viral molecules to viral particles includes long-chain fatty acids, such as palmitic acid. Fatty acids are readily coupled, through a variety of reactions, to anti-ligands; are readily diffused into viral membranes; and can be added to viral lipid membranes at a relatively high molar concentration without reducing the lytic activity of the virus. Palmitic acid lipid moieties are employed in the hemolytic particle preparations described in Examples I and II.

The hemolytic particles formed in accordance with above methods may be stored at refrigerator temperatures for up to several months or more without loss of lytic activity. In fact, studies conducted in support of the application show that the hemolytic activity of the particles may increase substantially after a several-week storage period at refrigerator temperature. A comparison of the data from studies reported in Examples XIII–XV shows that maximum lytic activity of hemolytic particles containing surface-bound anti-phthalate antibodies increases, over a several-day storage period at 4° C., from about 40% to nearly 100% of the total possible lytic activity.

A similar enhanced lytic activity is also observed in particles formed from viruses which have been frozen for an extended period, and can be achieved also by subjecting freshly prepared hemolytic particles to several freeze-thaw cycles, (Example VIII). Thus, one aspect of the preparation of the hemolytic particles of the invention may include storing the virus used in particle preparation for extended periods at freezer temperatures and/or subjecting the prepared particles to several freeze-thaw cycles.

II. Preparation of Target Cells

Lysable target cells for use in the immunoassay system of the invention include lipid bilayer cells, each encapsulating an aqueous space containing a reporter which is detectable upon cell lysis. These cells preferably include desialylated erythrocytes, or desialylated biological cell ghosts prepared from biological cells, such as erythrocytes. The cells may also include liposomes which have been prepared to include cholesterol, as described, e.g., in references 5. The target cells contain arrays of surface-bound, analyte-related binding molecules which function in the different immunoassays of the invention to bind the hemolytic particles to the target cells in proportion to the amount of analyte present. Characteristics of the analyte-related binding molecules and their mode of attachment to the target cells will be described below.

Methods for preparing desialylated erythrocytes are known (reference 4). One standard procedure, illustrated in Example III below, involves treating an erythrocyte suspension with neuraminidase, followed by extensive washing. The neuraminidase treatment is carried out until the cells show no appreciable agglutination or lysis when incubated with Sendai virus under cell-lytic conditions. As described in Example III, neuraminidase treatment at 37° C. for 60 minutes reduced the susceptibility of erythrocytes to virus-mediated lysis to less than about 1% of the level observed with untreated erythrocytes.

Biological cells which are suitable for use in preparing target cells include a variety of cells having surface-bound sialic acid antigens which render the cells susceptible to binding and lysis by hemolytic viruses. Cell ghosts, such as erythrocyte ghosts, can be prepared from such cells by a number of known methods. In one preferred method, described in Example VI, washed erythrocytes are subjected to slow dialysis against a hypotonic buffer, and reannealed in an isotonic saline solution containing a selected reporter at 37° C. Preferred types of reporters which can be encapsulated in the ghosts during reannealing are described below. Rapid osmotic shock or drug-induced cell lysis are other methods which may be suitable for forming biological ghosts. The erythrocytes or ghosts are treated with neuraminidase to remove surface accessible sialic acid residues, substantially as described above.

Properties of and methods for preparing liposomal target cells which are susceptible to viral-mediated lysis are described generally in reference 5. If glycophorin is added to the liposomes it is necessary to treat the glycophorin, either before or after its incorporation into the liposomal bilayer membrane, by neuraminidase to remove the sialic acid residues by which the cells could otherwise interact with HN and F hemolytic particle proteins.

Characteristics of the analyte-related molecules attached to the target cell surfaces will now be considered, first with respect to the sandwich-type reaction of the invention. As indicated above, the analyte-related molecules and analyte molecules in the sandwich-type reaction are opposite members of a ligand/anti-ligand binding pair, which may be selected from any of the binding pairs described in section I. The only constraint on the selection of binding pairs is that the analyte, when bound to its target-cell binding pair, must also be accessible for specific ligand/anti-ligand binding with particle-bound anti-analyte. The analyte/target cell binding pair may be similar or identical to the analyte/particle binding pair as, for example, where the analyte is a bivalent antigen (ligand), and the target cell analyte-related and particle anti-analyte molecules include anti-antigen antibodies. Preferably the anti-analyte antibodies carried on the particles have different epitope specificity than those carried on the target cells, to prevent direct competition between the particles and cells for binding to specific analyte binding sites.

Alternatively, one of the analyte-binding species on the particles or target cells may include ligand-type molecules, and the other, anti-ligand molecules, as, for example, where the analyte-related target cell molecules are surface antigens, the analyte is an anti-antigen antibody, and the viral particle-bound anti-analyte molecules include antibodies against the analyte antibody. Target-cell analyte-related antigen molecules may be native (endogenous) target cell surface antigens, such as an erythrocyte surface antigen, or may be foreign (exogenous) antigens attached to the target cell surfaces, for example by lipid-moiety attachment. Example X illustrates an immunoassay in which the analyte-related molecules include endogenous erythrocyte D surface antigen, for determination of anti-D IgG analyte.

In the analyte-inhibition reaction of the invention, the analyte-related molecules on the target cells include foreign, analyte-like molecules which are capable of competing with the analyte for specific, high-affinity binding to the particle anti-analyte molecules. Typically, the anti-analyte includes an antibody or fragment thereof, and the analyte and analyte-like molecules include the corresponding antigen—either a hapten or a large protein antigen. Example VIII describes an analyte-inhibition immunoassay test for the determination of IgG analyte, where target-cell bound IgG competes with the analyte for binding to anti-IgG carried on the hemolytic particles. In the inhibition immunoassay described in Example XIV, cell-bound phthalate competes with phthalate analyte for binding to anti-phthalate antibody carried on hemolytic particles.

The analyte-related molecules carried on the target cells are also referred to in the competitive inhibition assay, as foreign binding molecules which are added to the cells to bind hemolytic particles to the cells, to initiate particle-mediated cell lysis. The foreign binding (analyte-related) molecules and the analyte are both members of a ligand/anti-ligand pairs whose opposite binding member is the particle-bound anti-analyte.

The methods described in Section I for attaching anti-analyte molecules to hemolytic particles are generally applicable to attaching the foreign (exogenous) analyte-related molecules to target cell surfaces. Lipophilic hapten molecules may be diffused directly into biological or biological ghost target cells or incorporated into the lipids of liposomal target cells. Water-soluble hapten or large biological molecules are preferably attached to the target cells by covalent attachment to suitable lipophilic anchors, such as those described in Section I. Although the analyte-related molecules may be attached directly to activated lipids which have been previously incorporated into the target cells, a preferred attachment method includes first derivatizing the analyte-related molecules with a suitable lipid, as described in Section I, and diffusing the analyte-related molecule/lipid conjugate into the target cell membrane, for example, by incubation in the presence of a dilute detergent.

The lipid which is attached to the analyte-related molecules is one which includes, or can be modified to include, a suitable reactive head, and which has suitable solubility characteristics for diffusion into target cells. It may also be advantageous to select a lipid which itself does not contain sialic-acid moieties which would themselves be capable of reacting with particle-bound HN glycoproteins to promote non-specific cell lysis. The results of the experiments reported in Example VII below indicate that target cells in which the analyte-related molecules are anchored by ganglioside lipid moieties (containing sialic acid) show a level of non-specific lysis which is approximately 25% that of maximum analyte-specific cell lysis.

In target cells prepared to contain exogenous analyte-related molecules, the surface concentration of ligand-related molecules is selected to ensure that an easily measured level of target-cell lysis is produced in the presence of a threshold level of analyte. Where the analyte-related molecules are covalently attached to surface-active lipids contained in the target cells, the surface concentration of the molecules can be varied according to reactant concentrations, and/or reaction conditions. Where the analyte-related molecules are first coupled to a lipid moiety, and then diffused into the target cells, the surface concentration of analyte-related molecules is readily adjusted according to the relative concentrations of target cells and lipid/molecule couples which are added together in the diffusion reaction. It will be seen in Example IV, describing diffusion of lipid-derivatized IgG molecules into erythrocyte target cells, that the surface concentration of attached molecules is roughly proportional to the concentration of conjugates added to the diffusion reaction. The effect of the surface concentration of analyte-related molecules on the extent of virus-mediated cell lysis on immunoassay test sensitivity will be considered in Section III below, and with reference particularly to Examples XII and XV.

The reporter or reporter molecules which are encapsulated in the target cells may be an endogenous reporter, such as hemoglobin in erythrocyte target cells, or an exogenous reporter which is encapsulated into target cell ghosts during cell formation. The advantage of non-chromophoric reporters whose release from lysed target cells can be detected readily in a suspension of the cells has been mentioned above. Such reporters include self-quenching fluorogenic compounds, and stable free radical compounds, such as nitroxide spin labels, whose spin coupling characteristics are highly concentration dependent. Exemplary fluorogenic compounds include 6-carboxyfluorescein (CF), 4-methylumbelliferyl phosphate, 2',7'-[bis(carboxymethyl-amino)fluorescein (calcein), and N-1-aminonapthalene-3,6,8-trisulfonate (ANTS). Exemplary stable free radicals include water-soluble nitroxide free radicals, such as those described in U.S. Pat. No. 3,887,698.

Enzyme reporters are preferably those whose activity can be measured readily spectrophotometrically or fluorometrically, in a target cell suspension. Representative classes of enzymes contemplated herein include oxidoreductases, typified by glucose oxidase, galactosidase and catalase; hydroxylases, typified by various phosphatases, such as alkaline phosphatase, glycoside hydrolases, such as beta-galactosidase; peptidases; and lipases. Expression of reporter enzymes upon cell lysis may occur either by release of the enzyme from the lysed cells, or by infusion of an extracellular substrate into the lysed cells. The latter mechanism may be relatively more important with large molecular-weight proteins.

Reporter molecules may be incorporated readily into biological ghost target cells by reswelling and reannealing washed ghosts in the presence of a solution of the reporter molecules, as illustrated in Example VI. Incorporating reporter molecules into liposomal-type target cells is accomplished by forming the liposomal target cells in the presence of a solution of the reporter molecules, as described generally in U.S. patent application for "Blood-Fluid Composition for Cell Lysis System" filed Feb. 23, 1984, Ser. No. 583,095, and assigned to the assignee of the present invention.

III. Viral Lysis Immunoassays

This section details procedures for determining the presence and/or quantity of a soluble analyte in the immunoassay system of the invention. Describing a sandwich-type immunoassay reaction first, the assay reaction is carried out in a suitable reaction medium whose pH and ionic strength are compatible both with ligand/anti-ligand binding (between the analyte and particle-bound anti-analyte, and between the analyte and analyte-related target cell molecules). Additionally, the pH and/or ionic strength may be adjusted to achieve desired surface charge characteristics on the target cells or hemolytic particles. The osmolarity of the reaction medium is preferably the same or slightly lower than that of the interior target cell spaces, to allow efficient viral-mediated cell lysis.

The concentration of target cells, and the surface concentration of analyte-related molecules on the cells in the assay reaction are preferably adjusted to levels at which addition of increasing amounts of analyte, in the concentration range of analyte to be tested, produces increasing cell lysis. Typically, the concentration of erythrocyte target cells ranges betwee about 1% and 2% (v/v) of the total assay volume, as illustrated generally in Examples VII–XV. As will be seen from Examples VII, XII and XV, the maximum exten of cell lysis producible in the immunoassay system increases with increasing surface concentrations of analyte-related molecules, up to a surface concentration of between about $2 \times 10^5$ analyte-related molecules per erythrocyte target cell.

The concentration of hemolytic particles in the immunoassay system is preferably that which just produces maximal or near-maximal cell lysis in the general analyte concentration range to be assayed. The particle concentration can be determined readily by titrating a reaction mixture with increasing amounts of virus particles, until maximal or near maximal lysis is achieved. Example X below demonstrates that addition of increasing amounts of virus particles, up to a concentration of about 0.36 ug viral protein per microliter, produces increasing amounts of target cell lysis. Interestingly, the level of target cell lysis observed was substantially independent of the concentration of anti-analyte molecules carried on the virus particles, in the range between about 20 and 100 ug anti-analyte antibody per mg of virus.

In a typical sandwich-type immunoassay, such as the one described in Example X, target cells containing the surface-bound analyte binding molecules are preincubated either with buffer, for determination of non-specific lysis, or with the analyte, for determination of analyte-specific lysis. Following this preincubation, hemolytic particles are added, and the complete immunoassay reaction mixture is incubated further typically for about 20 minutes at 4° C., during which binding of the hemolytic particles to the target cells occurs, followed by additional incubation for about 30 minutes at 37° C., to promote particle/cell fusion and cell lysis. The analyte may also be incubated with target cells and lytic particles in a single step.

To determine percent reporter released from the target cells, the concentration of reporter in the assay mixture is determined, e.g., spectrophotometrically. This value is then compared with total releasable marker determined by adding a cell lytic agent, such as a detergent, to the complete assay mixture, to release virtually all of the encapsulated reporter. The percent release may further be corrected for background reporter level not related to the presence of hemolytic particles by measuring the extent of cell lysis observed in an assay mixture which does not contain added hemolytic particles. Example III below describes the quantitation of cell lysis in a reaction system containing erythrocyte target cells. In this system, it was necessary first to remove erythrocyte target cells by centrifugation before measuring released reporter. An immunoassay system in which released reporter is measurable spectrophotometrically in the presence of target cells is described in Example XVI.

The various considerations relating to assay medium, concentration of assay components, and methods for determining percent marker release discussed above with reference to the sandwich-type assay reactions are generally applicable to assays based on analyte-inhibition. One major distinction, however, is that the analyte-inhibition assay is typically performed by preincubating the analyte with the hemolytic particles, to "tie up" anti-analyte molecules on the particles in proportion to the amount of analyte present, followed by addition of target cells to the incubate. In the sandwich-type assay, as discussed above, the analyte is preferably first preincubated with target cells to coat the cells with the analyte, followed by addition of particles to the incubate to bind the particles to the cells in proportion to the amount of analyte present.

Example VIII below describes a cell lysis inhibition for determination of human IgG analyte. The assay was performed by first preincubating increasing concentrations of the analyte with hemolytic particles, cooling the virus/analyte mixtures to 4° C., and adding target cells to a final concentration of about 1%. After incubation at 4° C. for 20 minutes and 37° C. for 30 minutes, the percent cell lysis was measured. As will be seen in the example, the immunoassay system is responsive to changes in analyte concentration within the range of about 0.1 to 100 ug analyte per ml. A similar type of inhibition assay for soluble human IgG is described in Example XI, in which the effect of increasing particle anti-analyte concentrations was examined. The results from this example demonstrate that the extent of inhibition of viral-mediated cell lysis is substantially independent of the surface concentration of particle-bound anti-analyte molecules in the range examined. Example XII, which also involves an immunoassay for soluble human IgG, examines the effect of concentration of target cell analyte-related molecules on percent cell lysis analyte added to the system. The results of this experiment indicate that the absolute extent of cell lysis is greater in target cells having greater surface concentrations of analyte-related molecules, but that the relative degree of inhibition observed with the addition of increasing amounts of soluble analyte is substantially independent of this target cell surface concentration.

Example XIV describes a cell-lysis inhibition assay for determination of soluble phthalate in an immunoassay system where the analyte competes with target-cell phthalate surface molecules for binding to anti-phthalate antibody carried on hemolytic particles. The assay is sensitive to as little as one nanomolar 4-aminophthalate, and can be used to quantitate analyte levels up to a maximum concentration of about 1 mM. The experiment reported in Example XV indicates that absolute cell lysis levels in the phthalate inhibition test are dependent on the target cell surface concentration of phthalate molecules, but that the relative inhibition of cell lysis observed with increasing amounts of phthalate analyte is substantially independent of this surface concentration, similar to the findings from Example XII mentioned above.

From the foregoing, it can be seen how various objects and advantages of the invention are achieved. The assay system described herein provides a convenient, easily performed immunoassay for determination of soluble analytes. The assay components are readily and inexpensively prepared, and can be tailored, in terms of target cell and hemolytic particle surface molecules, for use in determining a wide variety of monovalent or multivalent analytes. The assay components are stable on storage, and in fact, the hemolytic particles appear to increase in lytic activity under certain storage conditions.

The invention further includes a kit for the determination of an analyte in the immunoassay system described above. The kit includes hemolytic particles and target cells of the type described above. Surface arrays of foreign (exogenous) analyte-related molecules attached to the target cells are adapted to bind the analyte, or compete therewith for binding to particle-bound anti-analyte, to bind the particles to the cells in proportion to the amount of analyte present in an assay mixture containing the particles and cells. Another aspect of the invention includes a method for determination of the soluble analyte, carried out according to the procedures detailed above.

The following examples illustrate various aspects of the invention, but are in no way intended to limit the scope thereof.

EXAMPLE I

Preparation of Virus Particles

This example describes the preparation of hemolytic particles having a surface array of rabbit anti-human antibodies. Rabbit anti-human IgG antibody (AxIgG) was obtained from Cappel Laboratories (Cochranville, Pa.). The N-hydroxysuccinimide ester of palmitic acid (NHSP) was synthesized and purified by recrystallization from ethanol, as described in reference 13. 2 mg of AxIgG was added to 70.6 ug of NHSP, corresponding to a molar NHSP:antibody ratio of 15:1, in phosphate buffered saline (PBS) containing 2% deoxycholate (DOC). PBS contained 140 mM NaCl, 20 mM $Na_2HPO_4$, 2mM EDTA, pH 7.4. The reaction mixture was incubated for 10–14 hours at 37 °C. and then chromatographed on a Sephadex G-75 column in PBS containing 0.15% deoxycholate to remove unreacted reagents. The void volume containing the antibody/palmitic acid conjugate (AxIgG/PA) was collected and concentrated by ultrafiltration.

Sendai virus (Z strain) were grown in the allantoic sac of 10- or 11-day chicken eggs, substantially as described in reference 15, and stored frozen ($-20°$ C.) for about three months before use. The AxIgG/PA conjugate (204, 100 or 42 ug antibody protein) was incubated with Sendai virus (1 mg of viral protein) in 1 ml PBS containing 0.012% DOC overnight at room temperature. The virus was washed three times with 1 ml PBS, and centrifuged with each washing step, to remove antibody not associated with the virus. Table I below shows, for each of the three initial AxIgG/PA concentrations added, the final ratio of antibody to virus, expressed in ug of derivatized antibody/mg of viral protein. As seen from the data, approximately 50% of the added antibody was incorporated into the virus.

TABLE I

| Initial AxIgG/PA ug AxIgG | final AxIgG:virus (ug:mg) |
|---|---|
| 204.1 | 108.0 |
| 100.0 | 54.3 |
| 42.3 | 19.3 |

EXAMPLE II

Preparation of Anti-Phthalate Virus Particles

This example describes the preparation of Sendai virus having surface-bound anti-phthalate antibody (AxP) anchored to the viral membrane by palmitic acid covalently attached to the antibody. Rabbit anti-phthalate antibody was prepared and partially purified by immunological procedures. The antibody (2 mg) was mixed with 70.6 ug of NHSP in 12 microliters of dioxane, prepared as described in Example I, in a total volume of 371 microliters of PBS containing 2% DOC. The mixture was incubated at 37° C. for 10–15 hours and then chromatographed by molecular sieve chromotography in the presence of 0.15% DOC to remove unreacted NHSP.

The anti-phthalate antibody/palmitic acid (AxP/PA) conjugate was resuspended in PBS containing 0.15% DOC to a final concentration of 484 ug per ml. Sendai virus was prepared as in Example I, and stored frozen (−20° C.) for about three months before use. The virus was washed 3 times in PBS, with centrifugation, and resuspended in PBS to a final concentration of 5 mg viral protein per ml.

417 microliters of the AxP/PA conjugate were added to 1 ml of the washed Sendai virus, and PBS and concentrated DOC (5.19%) were added to a final volume of 5 milliliters. The mixture (containing 0.012% DOC) was incubated overnight at room temperature. The virus was washed 3 times with PBS, with centrifugation, to remove unbound conjugate. Approximately 15% to 30% of the total AxP/PA added to the virus was incorporated into the viral membrane, giving a surface concentration of about 6–12 ug antibody per mg viral protein.

EXAMPLE III

Preparation of Desialylated RBC Target Cells

Freshly drawn human erythrocytes were washed 3 times with PBS and suspended in Tris/saline buffer containing 10 mM Tris/HCl, 20 mM $CaCl_2$ and 150 mM NaCl, pH 7.4, to form a 20% erythrocyte suspension. 1 ml of the suspension was incubated with 1 ml of *Vibrio cholerae* neuraminidase obtained from Cal Biochem (LaJolla, Calif.) and suspended in Tris/saline buffer to 1 unit per ml. The neuraminidase treatment was carried out for 60 minutes at 37° C., after which the desialylated cells were washed 4 times with PBS buffer.

The extent of erythrocyte hemolysis produced by incubating the neuraminidase-treated cells with Sendai virus was examined in a hemolysis assay performed substantially in accordance with reference 16. Briefly, 25 microliters of virus suspension (between 2 and 3 mg viral protein per ml) was mixed with either neuraminidase-treated or untreated erythrocytes (each a 20% solution) in a final volume of 125 microliters. The reaction mixture was allowed to stand on ice for 20 minutes, to promote binding of the virus to the erythrocytes, then incubated at 37° C. for 30 minutes, to produce erythrocyte lysis. After the incubation, 0.4 ml of PBS was added and the mixture centrifuged at 300×g for 5 minutes to pellet the erythrocytes. The entire supernatant was carefully removed, and the optical density of the released hemoglobin at 540 nm was measured. To measure total releasable hemoglobin, an identical reaction mixture, incubated under the conditions just described, was diluted with 0.4 ml PBS, and concentrated Triton X-100 was added, to a final concentration of 0.1% Triton, to produce complete red blood cell lysis, and the optical density of this lysed mixture was measured at 540 nm. Percent hemoglobin release was calculated by dividing the sample OD by the total releasable hemoglobin OD. The percent hemoglobin release by incubating neuraminidase-treated erythrocytes with Sendai virus was less than 1% of the total releasable marker, whereas untreated erythrocytes showed nearly 100% hemoglobin release. The results of this study show that neuraminidase treatment removed substantially all of the surface sialic acid residues required for viral lysis.

EXAMPLE IV

Preparation of RBC Target Cells with Surface-Bound Human IgG

This example describes the preparation of desialylated. human red blood cells containing surface-bound human immunoglobulin G (IgG) molecules. Desialyated D-antigen human erythrocytes were prepared in accordance with Example III using red cells which were D-antigen positive.

Mixed brain gangliosides, obtained from Sigma Chemical Company (St. Louis, MO), were oxidized by periodate, according to the method of Heath, et al. (reference 7). The oxidized gangliosides were separated from the other reactants by chromotography on a column of Sephadex G-25, and were lyophilized and resuspended to a concentration of 1 mM in chloroform/methanol (1:1).

Human IgG was purchased from Cappel Laboratories (Cochranville, PA), and was suspended in PBS to a concentration of 5 mg/ml. 1 ml of the IgG solution was added to 1 micromole of dried oxidized ganglioside, and the mixture was incubated overnight at room temperature in the presence of 0.01 M recrystallized sodium cyanoborohydride, substantially as described in reference 7. The IgG-ganglioside (IgG/G) conjugates were then adjusted to a final concentration of 5 mg conjugate per ml.

A 4% solution of desialylated RBC's was incubated with either 100, 200, 500 or 1,000 mg IgG/G conjugate in a total volume of 500 microliters, for 4 hours at 37° C. The unincorporated material was removed by several washing steps with centrifugation. The amount of cell-bound human IgG was determined by including small amounts of radiolabeled hIgG in the protein used in forming the IgG/G conjugates. These values are shown in TABLE II below, along with the calculated ratio of molecules of human IgG per red blood cell for each of the different IgG/G reactant concentrations shown in the left-hand column in TABLE II.

TABLE II

| Ab-G (ug) | bound IgG/G (ug) | IgG/G per RBC (molecules/cell) |
|---|---|---|
| 100 | 1.6 | $3.90 \times 10^4$ |
| 250 | 3.3 | $8.41 \times 10^4$ |
| 500 | 6.0 | $15.1 \times 10^4$ |
| 1000 | 10.5 | $26.3 \times 10^4$ |

As seen from the table, the surface concentration of IgG on the desialylated RBC's is roughly proportional to the initial concentration of IgG/G added to the RBC's.

EXAMPLE V

Preparaton of RBC Target Cells with Surface-Bound Phthalate

A third type of desialylated target cell was prepared by diffusing 4-amino-phthalic acid (AP) into the surface of desialylated red blood cells, using an amino phthalate-ganglioside (AP/G) conjugate. AP was obtained from Alfa Products (Danvers, MA). 6 micromoles of AP were incubated with 1 micromole of oxidized ganglioside, prepared in accordance with Example IV, in 1 ml of PBS in the presence of 0.01 M sodium cyanoborohydride. The reaction was allowed to proceed overnight at room temperature, forming an AP/G conjugate preparation.

Desialyated RBC's, (20 microliters packed cells) prepared as in Example II, were incubated with either 120, 300, 600 or 1,200 nanomoles of the AP/G conjugate in a total volume of 500 microliters, for 4 hours at 37° C. The cells were washed several times with PBS by centrifugation to remove free Ap-G conjugate. The different target cell preparations were stored at 4° C. until used.

EXAMPLE VI

Preparation of Erythrocyte Ghost Target Cells

This example describes the preparation of erythrocyte ghost target cells encapsulating a fluorogenic reporter. Calcein or (2',7'-[bis (carboxymethyl-amino)]-fluorescein), was obtained from Sigma Chemical Company (St. Louis, Mo.). Freshly drawn D-antigen human erythrocytes were resuspended in a phosphate-buffered saline containing 20 mM sodium phosphate, 140 mM sodium chloride, pH 7.4 to a final concentration of 100 microliters packed cells per ml of buffer. A portion of the cells were treated with neuraminidase to remove surface-exposed sialic acid residues, substantially according to the method described in Example III.

The resuspended cells were dialyzed for 90 minutes at room temperature against 2 liters of 2 mM sodium phosphate, 14 mM sodium chloride, pH 7.4 to produce slow-dialysis lysis. The lysed cells were pelleted by centrifugation at 10,000 rpm for 10 minutes and resuspended in 2 ml solution of 38 mM calcein, pH 7.2 having an osmolality adjusted to 290 mosm with sodium chloride. Following 15 minute equilibration on ice, and 60 minute incubation at 37° C. to promote reannealing of the membrane, the ghosts were washed free of calcein by repeated centrifugation and resuspension in isotonic phosphate-buffered saline, pH 7.4.

To determine the susceptibility of calcein-loaded ghosts to viral lysis, 0.5 ml of the calcein-loaded ghosts (prepared from cells with intact surface glycophorin) were diluted to the concentration which produced an appropriate fluorescence signal when measured using a Perkin-Elmer 60-50 10S fluorometer, at an excitation wavelength of 493 nm and an emission wavelength of 514 nm. The diluted ghosts were incubated with an equal volume of PBS containing Sendai virus for one hour at room temperature. The Sendai virus were present at concentrations produced by diluting the virus (4 mg protein/ml) 1:1, 1:2, 1:4, 1:8 and 1:16 with PBS. Specific release of fluorescent marker was determined from the fluorescent signal and calculated from the following formula:

$$\% \text{ specific release} = \frac{F_e/F_{e\,tot} - F_o/F_{o\,tot}}{1 - F_o/F_{tot}} \times 100$$

where $F_e$ equals the fluorescence in the presence of virus, $F_{e\,tot}$ is the reading in the presence of virus after the addition of a cell-lysing detergent, $F_o$ is the reading in the absence of virus, and $F_{tot}$ is the reading in the absence of virus after the addition of the detergent. As seen from the data in TABLE III below, increasing amounts of virus in the lysis reaction mixture produced increasing percent marker release, up to a maximum of about 89% marker release at the highest virus concentration. Specific release from desialylated calcein-loaded ghosts, under substantially the same incubation conditions, produced negligible virus-specific marker release (less than about 3%).

TABLE III

| viral dilution | % marker release |
|---|---|
| 1:1 | 89 |
| 1:2 | 82 |
| 1:4 | 66 |
| 1:8 | 48 |
| 1:16 | 31 |

The surface specificity of viral-mediated ghost lysis was confirmed in a lysis inhibition study in which increasing concentrations of fetuin, a sialic acid containing protein, were incubated with the native Sendai virus prior to the addition of the target ghost cells. In the absence of added fetuin, the percent specific lysis was about 99%, as determined by the above method. Addition of increasing amounts of fetuin progressively reduced the observed percent specific lysis, down to a level of about 15% lysis produced by target cells incubated in the presence of 2 mg per ml of fetuin.

EXAMPLE VII

Target Cell Lysis by Direct Virus/Target Cell Binding

This example examines the ability of Sendai virus containing surface-bound anti-human IgG antibody (AxIgG-virus) to lyse desialylated RBC's containing surface-attached human IgG. The target cell lysis assay was performed by mixing 25 microliters of virus suspension (40 mg viral protein per ml) prepared as in Example I, and stored one day at 5° C. before use, with 100 microliters of a 2 percent suspension of desialylated RBC's prepared either as in Example III (no surface-bound IgG), or as in Example IV, by incubation with one of the four different IgG surface concentrations shown at the left in TABLE IV below. Each reaction mixture was incubated for 20 minutes on ice followed by an incubation at 37° C. for 30 minutes. After incubation, each mixture was centrifuged to pellet the erythrocytes, and the percent lysis calculated as described in Example III. The results are shown in the second column from the left in TABLE IV. As seen, Sendai virus carrying surface-bound antibody produce substantially no lysis of erythrocytes which themselves do not contain surface-attached human IgG, but produce increasing amounts of cell lysis in target cells having increasingly greater surface concentrations of human IgG. Thus virus-mediated lysis is seen to require specific interaction between the exogenous virus Ab and exogenous target cell IgG antigens.

TABLE IV

| AxIgG/G (molecules/ cell × $10^4$) | % Lysis | | |
|---|---|---|---|
| | AxIgG- virus | Native virus | AxIgG- virus + IgG |
| 0 | 0 | 0 | 0 |
| 3.9 | 9.3 | 0 | 0.1 |
| 8.4 | 25.5 | 8.1 | 8.2 |
| 15.1 | 30.9 | 6.7 | 6.1 |
| 26.3 | 39.5 | 13.8 | 12.3 |

The five different target cell preparations were also incubated, under similar assay conditions, with native Sendai virus not containing surface-bound antibody, with the results shown in the second column from the right in TABLE IV. Here it is seen that erythrocytes having a surface concentration of greater than about $8 \times 10^4$ molecules per cell are susceptible to non-specific lysis by native Sendai-virus at a level which is approximately 25% of the specific lysis produced by Sendai virus containing surface-bound antibody.

Assays similar to those just described were performed by incubating each of the fiVe erythrocyte preparations with AxIgG-virus in the presence of a maximally inhibitory amount of soluble human IgG (determined from Example VIII below). The percent lysis observed for each of the five erythrocyte target cells, shown in the right hand column in TABLE IV, is substantially identical to the percent lysis observed for the assays containing native Sendai virus in the absence of soluble human IgG. The two control assay groups indicate that specific IgG/anti-IgG binding is not responsible for the observed non-specific lysis, which therefore may be due to binding between native virus binding molecules and sialic acid residues in the target cell IgG/ganglioside conjugates.

EXAMPLE VIII

Viral Lysis Inhibition Assay for Determination of Human IgG

This example describes an assay procedure for the determination of soluble human IgG, based on inhibition of antibody-specific, viral-mediated target cell lysis. Sendai virus (AxhIg-virus) having surface bound anti-human IgG antibody were prepared as in Example I. Target cell erythrocytes having a surface concentration of exogenous human IgG of about $8 \times 10^4$ molecules per cell were prepared as described in Example III. AxIgG-virus (final concentration, 0.5 mg/ml) was incubated with the various concentrations of human IgG (expressed in ug per ml) shown at the left in TABLE V below, in a total volume of 75 microliters, for 10 minutes at room temperature. The virus/IgG mixtures were then cooled to 4° C., and 100 microliters of a 2% suspension of the erythrocytes were added to each mixture. The assay suspensions were incubated at 4° C. for 20 minutes, followed by incubation for 30 minutes at 37° C. The percent lysis, shown below in the right-hand table in TABLE V, was determined for each assay substantially as described in Example III.

TABLE V

| hIgG (ug/ml) | % lysis |
|---|---|
| 0 | 39 |
| .143 | 31 |
| 1.43 | 23 |
| 14.30 | 15 |
| 143.00 | 12 |

As seen from the data, increasing the amounts of added IgG produced increasing inhibition of target cell lysis. The range of inhibition, from a high of about 40% to a low of about 12% lysis, is consistent with the data reported in the right-hand column of TABLE III in Example V above.

EXAMPLE IV

Effect of Freeze/Thaw Tretament of Ab-Virus on Target Cell Lysis

AxIgG-virus, freshly prepared in accordance with Example I, (3.2 mg/ml) was subject to up to 15 cycles of freezing, by contact with a dry ice:propanol mixture, and thawing, in a water bath at room temperature, and the hemolytic activity of the virus after 2, 5, 10 and 15 freeze/thaw cycles was examined, substantially as described in Example III. Briefly, 25 microliters of the AxIgG-virus mixed with 25 microliters PBS was added to 100 microliters of 2% suspension of target cells prepared to contain a surface concentration of about $8 \times 10^4$ IgG molecules/cell (Example IV), and the mixture was incubated first for 20 minutes at 4° C., then for 30 minutes at 37° C. The percent lysis values, calculated as in Example III, are shown in TABLE VI. The lower 17% value compares with the 25% lysis value observed in Example VII above, for virus-mediated lysis of erythrocytes having about $8 \times 10^4$ IgG molecules/cell.

TABLE VI

| F/T cycles | % lysis |
|---|---|
| 0 | 17 |
| 2 | 28 |
| 5 | 29 |
| 10 | 34 |
| 15 | 39 |

Freeze-thawed virus did not cause lysis of desialylated RBC, indicating that the freeze-thaw treatment did not lead to non-specific cell lysis.

From the data, it is seen that repeated freeze/thaw treatment increased the specific hemolytic activity of the virus to maximum hemolytic activity of about 40%, even at a relatively low antigen concentration on target cells.

EXAMPLE X

Viral Lysis Assay for Human Anti-D Antibodies

This example describes a sandwich-type viral lysis assay in which the analyte, human anti-D antibody, is adapted to bind immunospecifically to target-cell antigen, and to an exogenous viral anti-analyte, to bind the virus to the cell surface, to produce target cell lysis in proportion to the amount of analyte present. AxIgG virus prepared to contain each of the three antibody concentrations shown in TABLE I were prepared in accordance with the procedures described in Example I. Desialylated RBC's having endogenous surface antigen-D molecules were prepared as described in Example III. The source of the anti-D antibody analyte was fresh human anti-D antiserum obtained from healthy donors.

Each assay was performed by first sensitizing a 5% suspension of target cell RBC's with an equal volume of the human anti-D antiserum, diluted 1:1 with PBS, for 15 minutes at 37° C. The sensitized RBC's were washed 2 times with PBS, with centrifugation, and resuspended in PBS to form a 2% cell suspension. AxIgG-virus containing either 19, 54, or 108 ug Ab/mg viral protein, was added to 100 microliters of the 2% suspension of sensitized target cells, in a final volume of 150 microliters, and to the final viral concentration, expressed in ug viral protein/microliter of assay mixture shown in the left-hand column in TABLE VII below. Each assay mixture was incubated for 20 minutes at 4° C., followed by incubation for an additional 30 minutes at 37° C. Percent cell lysis, which is shown in TABLE VII for the AxIgG assays containing the lowest surface concentration of antibody (middle column) and the highest surface antibody concentration (right-hand column) were determined as in Example III.

TABLE VII

| viral protein (ug/ul) | % lysis AxIgG-virus (19 ug AxIgG/mg virus) | AxIgG-virus (108 ug AxIgG/mg virus) |
|---|---|---|
| 0 | 0 | 0 |
| .09 | 1.9 | 4.1 |
| .18 | 8.9 | 8.7 |
| .36 | 24.4 | 25.1 |

As seen from the data, target cells which were sensitized by incubation with the IgG analyte showed an extent of target cell lysis which is substantially proportional to the amount of Ab-virus added to the assay mixture, but not appreciably dependent on viral antibody surface concentration in the range tested. The extent of cell lysis observed in control target cells not sensitized with anti-D antibody analyte was less than five percent.

EXAMPLE XI

Viral Lysis Inhibition Assay for Soluble Human IgG

This example describes a viral lysis inhibition assay for determination and quantitation of soluble human IgG. AxIgG-Sendai virus preparations having each of the 3 different antibody surface concentrations indicated in TABLE I were prepared as described in Example I. Desialyated RBC's were sensitized with human anti-D IgG antibodies as described above in Example X. Soluble human IgG, was obtained from Cappel Laboratories, (Cochranville, Pa.).

Inhibition assays were performed by first incubating 25 microliters of each of the 3 different AxIgG-virus preparations with either buffer or human IgG, at one of the four different IgG concentrations indicated at the left in TABLE VIII below, in a final volume of 50 microliters. Following an approximately 5 minute incubation period at room temperature, 100 microliters of a 2% suspension of target cells, sensitized with anti-D antibody as in Example X, were added to each assay tube, and the assay mixture was incubated first for 20 minutes at 4° C., then for 30 minutes at 37° C. The percent target cell lysis, calculated as in Example III, is shown for the lowest and highest surface concentration of viral antibody in the center and right columns in TABLE I, respectively.

TABLE VIII

| sol. hIgG (mg/ul) | % lysis Ab-virus (19 ug AxIgG/mg virus | Ab-virus (108 ug AxIgG/mg virus) |
|---|---|---|
| 0 | 23.9 | 23.9 |
| 0.17 | 18.3 | 19.8 |
| 1.7 | 5.8 | 9.3 |
| 17 | 3.5 | 0.9 |
| 170 | 1.1 | 1.1 |

The data in TABLE VIII demonstrate that increasing concentrations of soluble IgG analyte in the assay mixture can be quantitated according to measured percent viral lysis, ranging from a high percent lysis of about 25%, in the absence of added IgG analyte, to substantially complete inhibition of viral lysis observed for an analyte concentration greater than about 17 ug per ml. The absolute percent lysis values were substantially independent of viral antibody concentration, within the range of surface antibody concentrations examined.

EXAMPLE XII

Effect of Target Cell Antigen Concentration on Inhibition of Viral Lysis

The present example is concerned with the effect of the surface concentration of target cell IgG on the extent of inhibition of viral lysis by soluble IgG. AxIgG-virus having an AxIgG surface concentration of about 108 ug antibody per mg viral protein were prepared as described in Example I. Desialylated D-antigen positive RBC's, prepared according to Example II, were sensitized by incubating 2.4 ml of a 2.5% cell suspension with either 300 ug (25 ug/5 microliters packed cells) or 3,000 ug (250 ug/5 microliters packed cells) of human anti-D IgG for 15 minutes at 37° C. The cells were then washed 3 times with 3 ml PBS, with centrifugation. The amount of anti-D antibody bound to the washed cells, as determined by adding $^{125}$I-labeled human anti-D IgG to the sensitization mixture, was determined to be about $4.7\times10^3$ molecules and $21.2\times10^3$ molecules per cell for the cell preparations sensitized by either 300 ug or 3,000 ug of anti-D IgG, respectively.

Viral lysis inhibition assays were performed, as in Example VIII, by first incubating 25 microliters AxIgG-virus (2.6 mg viral protein per ml) with different concentrations of soluble human IgG indicated in the left-hand column in TABLE IX below. The mixture, which was brought to a total volume of 50 microliters with PBS, was incubated for about 5 minutes at room temperature. After cooling the mixture to 4° C., 100 microliters of a 2% suspension of one of the two sensitized erythrocyte target cell preparations were added, and the assay mixture was incubated first for 20 minutes at 4° C., then for 30 minutes at 37° C. Percent target cell lysis, calculated as in Example III, is shown in the middle and right columns in TABLE IX for target cells having the lower and higher concentration of sensitizing IgG, respectively.

TABLE IX

| hIgG ($10^4\times$ ug/ml) | % lysis IgG-RBC ($4.7\times10^3$ AxIgG/cell) | IgG-RBC ($2.12\times10^4$ AxIgG/cell) |
|---|---|---|
| 0 | 14.7 | 25.2 |

TABLE IX-continued

| hIgG (10⁴ × ug/ml) | % lysis | |
|---|---|---|
| | IgG-RBC (4.7 × 10³ AxIgG/cell) | IgG-RBC (2.12 × 10⁴ AxIgG/cell) |
| 0.0017 | 15.0 | 24.5 |
| 0.017 | 16.6 | 24.4 |
| 0.17 | 12.7 | 18.8 |
| 1.7 | 3.5 | 8.5 |
| 17 | 1.4 | 3.7 |

As seen from the data, the two target-cell preparations employed in the example each showed about the same sensitivity to inhibition by soluble IgG, the percent lysis being inhibited at least about 6 fold over the IgG range from 0.017 to 17 ug per ml. The absolute amount of hemolysis, by contrast, is related to the surface concentration of target cell antigen (IgG) capable of reacting with the viral ligand antibody.

EXAMPLE XIII

Target Cell Lysis by Direct Virus/Target Cell Binding

The extent of antibody-specific target cell lysis produced by incubating AxP-virus (containing surface-bound anti-phthalate antibody) with target cells having various surface concentrations of surface-bound phthalate was investigated. AxP-virus containing a surface concentration of anti-phthalate antibody of about 143 ug antibody per mg viral protein were prepared as described in Example II, and suspended in PBS to a concentration of 2 mg viral protein per ml. Specifically, the particles were prepared from virus which had been stored frozen for 2 months, and after preparation, the particles were stored at 5° C. one day prior to use. Desialyated RBC target cells preparation containing increasing amounts of surface-bound phthalate were prepared as described in Example V, by incubating desialylated RBC's with either 120, 300, 600 or 1,200 nanomoles of AxP/G conjugate. The target cells are designated in the right-hand column of TABLE X below by the nanomolar amount of AxP/G conjugate used in their preparation.

25 microliters of the AxP-virus (2.0 mg viral protein/ml) were added to 100 microliters of a 2% suspension of each of the 5 different target cell preparations indicated, and the assay mixture was incubated first for 20 minutes at 4° C., then for 30 minutes at 37° C. The percent lysis values, calculated as in Example III, are shown in the second column from the left in TABLE X below. Here it is seen that target cells containing increasing amounts of surface-bound phthalate, up to the level produced by the addition of 600 nanomoles of AxP/G conjugate to 20 microliters of packed erythrocytes, were more susceptible to viral-mediated lysis. Of particular note is the fact that no measurable lysis was observed in desialylated target cell which did not contain surface-bound phthalate, indicating that substantially all of the lysis observed is mediated by AxP/phthalate binding between the virus and target cells.

A similar series of assays in which native washed Sendai virus (containing no surface-bound AxP) was performed to assess the level of non-specific target cell lysis due to interaction between the Sendai virus and the AP/G conjugate carried in the target cells. The assays, performed under conditions substantially identical to those described for the AxP-virus, gave the percent lysis data shown in the second column from the right in TABLE X. The data show increasing non-specific lysis as a function of target-cell AP/G conjugate concentration, up to a level about 20% of the corresponding specific lysis levels.

A third series of assays in which each of the 5 different target cell preparations described above were incubated with AxP-virus in the presence of an inhibitory amount of soluble AP was carried out. In each assay, 25 microliters of the AxP-virus from above was first incubated with 0.1 M AP in a final volume of 50 microliters for 5 minutes at room temperature. The AxP-virus/AP mixture was then added to 100 microliters of a 2% suspension of each of the 5 different target cell preparations, and the assay mixtures incubated first at 4° C. then at 37° C., as described above. The percent lysis data, shown in the right-hand column in TABLE X below, are substantially identical to the corresponding data from the assays employing control virus (containing no anti-phthalate antibody).

TABLE X

| target cell [AxP/G] (nmoles) | % lysis | | |
|---|---|---|---|
| | AxP-virus | Native virus | AxP-virus + AP |
| 0 | 0 | 0 | 0 |
| 120 | 26.0 | 0 | 2.0 |
| 300 | 36.9 | 5.3 | 7.0 |
| 600 | 45.6 | 9.5 | 10.3 |
| 1200 | 45.9 | 9.5 | 9.5 |

EXAMPLE XIV

Viral Lysis Inhibition Assay for AP Determination

The AxP-virus and target cell components described in Example XIII above were used in a viral lysis inhibition assay to quantitate soluble phthalate analyte. AxP-virus, at a concentration of 2.0 mg virus per ml, were prepared as described in Example II, and stored at 4° C. for 2 days before use. Desialyated erythrocyte target cells containing surface-attached AP were prepared as described in Example V, by incubating a 4% cell suspension with 600 nanomoles of AP/G conjugate. A solution of AP in PBS was added to 25 microliters of AxP-virus to produce the AP concentrations shown at the left in TABLE XI below, when the AP/AxP-virus mixture was brought to a final volume of 50 microliters with PBS. Following incubation of this mixture for about 5 minutes at room temperature, the mixture was added to 100 microliters of target cells (2 percent suspension), and the assay components were incubated first at 4° C., then at 37° C. as described above. Percent lysis values, calculated as in Example III, are shown in the right-hand column in TABLE XI.

TABLE XI

| AP (mM) | % lysis | |
|---|---|---|
| 0 | 66.3 | 5.7 |
| $10^{-6}$ | 65.6 | 4.0 |
| $10^{-5}$ | 60.6 | 0.6 |
| $10^{-4}$ | 53.8 | 2.1 |
| $10^{-3}$ | 57.6 | 4.0 |
| $10^{-2}$ | 33.3 | 3.0 |
| $10^{-1}$ | 12.0 | 3.0 |
| 1 | 14.1 | 0.8 |

From the data in the table above, it is seen that the inhibition assay procedure is sensitive to the presence of as little as ten nanomolar 4-amino-phthalate, and can be used to quantitate phthalate concentrations in the range between about 10 picomoles ($10^{-5}$ mm) and 0.1 mM. It is also of interest to note that maximum percent lysis achieved in the absence of added phthalate is about 65%, as compared with the 45% maximum lysis level observed in the assay involving PAb-virus described in Example XII above. This result is discussed below in Example XV.

EXAMPLE XV

Effect of Target Cell AP Concentration on Viral Lysis Inhibition Assay

The effect of target cell AP surface concentration on the viral lysis inhibition by AP was investigated. Target cell erythrocytes prepared by incubation with 120 or 600 nanomoles of AP/G conjugate were prepared substantially as described in Example V. AxP-virus containing surface-bound anti-phthalate antibody were prepared as in Example II, but were stored for 5 days at 5° C. prior to use, rather than for 1 and 2 days as in Examples XIII and XIV, respectively. The assays were performed substantially as described in Example XIV, by first incubating 25 microliters of AxP-virus (2.7 mg viral protein/ml) with 25 microliters of soluble AP, at one of the AP concentrations indicated in the left-hand column in TABLE XII below, for 5 minutes at room temperature. Following this incubation period, the AxP-virus/AP mixture were added to 100 microliters of a 2% suspension of one of the two target cell preparations, and the assay components were incubated first for 20 minutes at 4° C., then for 30 minutes at 37° C. Percent target cell lysis was calculated as described in Example III. Data showing the phthalate-dependent inhibition of cell lysis in target cells having the lower and higher surface concentration of bound phthalate are shown in the middle and right columns in TABLE XII, respectively.

The data indicate that both target cell preparations show about the same extent of relative inhibition in the phthalate range between about $10^{-5}$ and 1 mM, similar to the results reported in Example XIV above. Surprisingly, the percent lysis of target cells having the higher surface concentration of phthalate was close to 100% at soluble phthalate concentrations below about $10^{-4}$ mM. This substantially complete cell lysis contrasts with the maximum percent cell lysis of about 65% observed in Example XIV and about 45% observed in Example XIII. The different maximum percent lysis values apparently are due to the greater lytic activity of the AxP-virus which occurs upon storage at 4°-5° C., since the Ab-virus used in Example XIII had been stored for 1 day and that used in the present example had been stored for 2 days only. The substantially complete cell lysis observed here indicates that phthalate/anti-phthalate binding system appears to be substantially more efficient in producing cell lysis than the IgG/anti-IgG system, reported above, under the experimental conditions employed.

TABLE XII

| phthalate (mM) | % lysis | |
|---|---|---|
| | AP/G-RBC | 5 × AP/G-RBC |
| 0 | 63.9 | 96.2 |
| $10^{-6}$ | 68.1 | 96.2 |
| $10^{-5}$ | 66.1 | 90.5 |
| $10^{-4}$ | 66.5 | 95.8 |
| $10^{-3}$ | 49.5 | 88.2 |
| $10^{-2}$ | 29.1 | 66.5 |
| $10^{-1}$ | 16.7 | 40.3 |
| 1 | 11.6 | 31.6 |

EXAMPLE XVI

Viral Lysis Assay for Human Anti-D Antibodies

The assay described in this example is similar to the one described in Example X, except that the target cells are composed of desialylated calcein-loaded erythrocyte ghosts, rather than desialyalated erythrocytes. Sendai virus having surface-bound rabbit anti-human IgG antibodies (AxIgG-virus), were prepared in accordance with the procedures described in Example I. Desialylated, calcein-loaded erythrocyte ghosts having endogenous surface D antigens were prepared as described in Example VI.

A series of assays were performed by sensitizing an approximately 10% suspension of the calcein-loaded ghosts with an equal volume of human anti-D immunoglobulin (Example X), at one of several different concentrations, for 15 minutes at 37° C. The sensitized ghosts were washed 2 times with PBS, with centrifugation, and resuspended in PBS to form a 1% cell suspension. AxIgG-virus prepared as in Example I to contain approximately 50 ug antibody (against anti-D antibody) per mg of viral protein was added to 20 microliters of each of the sensitized 1% ghost suspensions, in a final assay volume of 50 microliters, and a final virus concentration of about 0.36 ug viral protein per microliter. Each assay mixture was incubated for 30-60 minutes at 37° C. Percent cell lysis, corrected for non-specific lysis in the absence of added virus particles, was calculated according to the method described in Example VI. The results show that increasing amounts of anti-D antibody analyte used in sensitizing the ghosts lead to increasing percent specific release of entrapped calcein.

While preferred embodiments of the invention have been described herein, it will be appreciated that various changes and modifications may be made without departing from the spirit of the invention.

What is claimed is:

1. A method for the determination of a soluble analyte comprising
   providing hemolytic virus particles having a lipid bilayer surface, surface-bound HN and F paramyxovirus proteins, and a surface array of non-viral, anti-analyte molecules composed of an anti-analyte which is not reactive toward red blood cell antigens and which is derivatized with a lipid moiety which anchors the molecules to the particle bilayer surfaces,
   providing lysable target cells which (a) are substantially devoid of surface receptors capable of binding to such HN or F proteins, (b) have surface bound exogenous, analyte or analyte analogue molecules which are anchored to the target cell surfaces through a lipophilic moiety, and are effective to compete with the analyte for specific binding to such anti-analyte molecules, thereby by initiate target cell lysis, and (c) contain an encapsulated reporter which is detectable upon cell lysis,
   reacting the analyte with the hemolytic particles and the target cells, to bind virus particles to the cells in inverse proportion to the amount of analyte present, and
   determining the extent of cell lysis produced as a result of said reacting, as evidenced by the extent of reporter release.

2. The method of claim 1, wherein providing such particles includes covalently coupling anti-analyte molecules to molecules of a fatty acid, to form anti-analyte/fatty acyl couples, incubating the couples with Sendai virus, and by said incubating, attaching the anti-ligand to the particle surfaces.

3. The method of claim 2, wherein said coupling includes reacting an anti-analyte antibody or antibody fragment with the N-hydroxysuccinimide ester of a fatty acid.

4. The method of claim 3, wherein said coupling includes reacting a mixture of antibodies containing between about 5 and 10 mole percent anti-analyte antibodies with the fatty acid.

5. The method of claim 1, wherein providing the viral particles includes freezing and thawing the particles repeatedly.

6. The method of claim 1, wherein providing the viral particles includes freezing virus precursors of the particles for an extended period of at least several days.

* * * * *